(12) United States Patent
Mast et al.

(10) Patent No.: US 7,700,750 B2
(45) Date of Patent: Apr. 20, 2010

(54) CONNEXIN ALLELE DETECTION ASSAYS

(75) Inventors: Andrea L. Mast, Oregon, WI (US); Erin Dorn, Cross Plains, WI (US); Robert W. Kwiatkowski, Jr., Verona, WI (US); Molly Accola, Madison, WI (US); Susan S. Wigdal, Madison, WI (US)

(73) Assignee: Third Wave Technologies, Inc., Madison, WI (US)

( * ) Notice: Subject to any disclaimer, the term of this patent is extended or adjusted under 35 U.S.C. 154(b) by 1127 days.

(21) Appl. No.: 10/754,408

(22) Filed: Jan. 9, 2004

(65) Prior Publication Data

US 2004/0203035 A1    Oct. 14, 2004

Related U.S. Application Data

(60) Provisional application No. 60/438,963, filed on Jan. 9, 2003.

(51) Int. Cl.
  C07H 21/02    (2006.01)
  C07H 21/04    (2006.01)
  C12Q 1/68     (2006.01)
  C12P 19/34    (2006.01)

(52) U.S. Cl. .................. 536/23.1; 536/24.3; 435/6; 435/91.1

(58) Field of Classification Search .................. None
  See application file for complete search history.

(56) References Cited

U.S. PATENT DOCUMENTS

| | | | |
|---|---|---|---|
| 5,614,402 A | 3/1997 | Dahlberg et al. | |
| 5,795,763 A | 8/1998 | Dahlberg et al. | |
| 5,843,669 A | 12/1998 | Kaiser et al. | |
| 5,846,717 A | 12/1998 | Brow et al. | |
| 5,912,340 A | 6/1999 | Kutyavin et al. | |
| 5,985,557 A | 11/1999 | Prudent et al. | |
| 5,994,069 A * | 11/1999 | Hall et al. ........ | 435/6 |
| 5,998,147 A * | 12/1999 | Petit et al. ........ | 435/6 |
| 6,001,567 A | 12/1999 | Brow et al. | |
| 6,001,983 A | 12/1999 | Benner | |
| 6,090,543 A | 7/2000 | Prudent et al. | |
| 6,090,606 A | 7/2000 | Kaiser et al. | |
| 6,194,149 B1 | 2/2001 | Neri et al. | |

(Continued)

FOREIGN PATENT DOCUMENTS

WO    WO97/27214    7/1997

(Continued)

OTHER PUBLICATIONS

Lyamichev et al; Nature Biotechnology, vol. 17, pp. 292-296; 1999.*

(Continued)

*Primary Examiner*—Jehanne S Sitton
(74) *Attorney, Agent, or Firm*—Casimir Jones, S.C.

(57) ABSTRACT

The present invention provides compositions and methods for the detection and characterization of mutations associated with non-syndromic hearing impairment. More particularly, the present invention provides compositions, methods and kits for using invasive cleavage structure assays (e.g. the INVADER assay) to screen nucleic acid samples, e.g., from patients, for the presence of any one of a collection of mutations in the Connexin 26, or gap junction beta 2, gene associated with non-syndromic hearing loss.

11 Claims, 4 Drawing Sheets

U.S. PATENT DOCUMENTS

| | | |
|---|---|---|
| 6,348,314 B1 | 2/2002 | Prudent et al. |
| 6,458,535 B1 | 10/2002 | Hall et al. |
| 6,485,908 B1 | 11/2002 | Petit et al. |
| 6,759,226 B1 | 7/2004 | Ma et al. |
| 2003/0104378 A1 | 6/2003 | Allawi et al. |
| 2003/0186238 A1 | 10/2003 | Allawi et al. |

FOREIGN PATENT DOCUMENTS

| | | |
|---|---|---|
| WO | WO98/23774 | 6/1998 |
| WO | WO98/42873 | 10/1998 |
| WO | WO98/50403 | 11/1998 |
| WO | WO01/98537 | 12/2001 |
| WO | WO02/070755 A2 | 9/2002 |
| WO | WO03/073067 A2 | 9/2003 |

OTHER PUBLICATIONS

Ahern, Holly; The Scientist, vol. 9, 1995, from the internet, pp. 1-5.*
ACMG, Genetics in Medicine, 4:162-171 (2002).
Allawi and Santalucia, Biochemistry, 36:10581-94 (1997).
Carrasquillo et al., Hum Mol Genet, 6:2163-2172 (1997).
Denoyelle et al., Hum Mol Genet, 6:2173-2177 (1997).
Doty et al., PNAS USA, 46:461 (1960).
Green et al., Gene Reviews (Feb. 12, 1999).
Green et al., JAMA, 281:2211-2216 (1999).
Guilford et al., Nat Genet, 6:24-8 (1994).
Hall et al., PNAS USA, 97:8272-8277 (2000).
Hudspeth, Science, 230:745-752 (1985).
Kelley et al., Am J Hum Genet, 62:792-799 (1998).
Kelley et al., Brain Research Reviews, 32:184-188 (2000).
Kenneson et al., Genetics in Medicine, 4:258-274 (2002).
Kong et al., Nucleic Acids Res, 17:10373-10383 (1989).
Kong et al., Nucleic Acids Res, 20:5149-5152 (1992).
Lee et al., PNAS USA, 88:2825-2829 (1991).
Lefebvre, Brain Research Reviews, 32:159-162 (2000).
Lyamichev et al., Nat Biotech, 17:292 (1999).
Marmur and Lane, PNAS USA, 46:453 (1960).
Mignon et al., Cytogenet Cell Genet, 72:185-6 (1996).
Moeller, Pediatrics, 106:3 e43 (2000).
Morell et al., New Engl J Med, 339:1500-1505 (1998).
Morton, in The Genetics of Hearing Impairment, The New York Acad Sci, New York, 630, 16-31 (1991).
Norton et al., Ear Hear, 21:529-535 (2000).
Reynaldo et al., The Kinetics of Oligonucleotide Replacement, J Mol Biol, 97:511-520 (2000).
Rossi et al., J Biol Chem, 257:9226-9229 (1982).
Schweitzer and Kool, J Am Chem Soc, 117:1863-1872 (1995).
Schweitzer and Kool, J Org Chem, 59:7238-7242 (1994).
Smith and Van Camp, Gene Reviews (Sep. 28, 1998).
Steel and Kros, Nat Genet, 27:143-149 (2001).
White, Brain Research Reviews, 32:181-183 (2000).
Wu et al., Genetics in Medicine, 4:279-288 (2002).
Yoshinaga-Itano et al., Pediatrics, 102:1161-1171(1998).
Zelante et al., Hum Mol Genet, 6:1605-1609 (1997).
Zhang and Nicholson, J Cell Biol, 109:3391-401 (1989).

* cited by examiner

Figure 4

5' cgcgccgagg cccaggatcgtct - Hex　　　　DM WT probe　　　　SEQ ID NO: 1
5' tccgcgcgtcc cccaggatcgtctg - Hex　　　SNP4b Del probe　　SEQ ID NO: 2

3' ctagaaaggttacgaccacctcacaaacaagtgggggtccagacagacgtcgcacggg 5'　　WT target　　SEQ ID NO: 4
3' ctagaaaggttacgaccacctcacaaacaagtgggggggtccagacagacgtcgcacggg 5'　Del target　SEQ ID NO: 5

5' tgctgtggagtgtttgttcacacca　　INVADER Oligonucleotide　　SEQ ID NO: 3

```
        tct    agccggt
      F   Q            t
5' cgcgccgaggc
Hex - gcgcggctccaga g  tcggcct
```

DM Fam FRET Cassette
SEQ ID NO: 6

```
        tct    agccggt
      R   Q            t
5' tccgcgcgtccc
Hex - aggcgcgcaggaga g  tcggcct
```

SEQ ID NO: 9

SNP4b Red FRET Cassette with Fam stem
SEQ ID NO: 7

SEQ ID NO: 8

CONNEXIN ALLELE DETECTION ASSAYS

The present application claims priority to U.S. Provisional Application Ser. No. 60/438,963, filed Jan. 9, 2003, which is incorporated herein by reference.

FIELD OF THE INVENTION

The present invention relates to compositions and methods for the detection and characterization of mutations associated with congenital hearing loss. More particularly, the present invention relates to compositions, methods and kits for using invasive cleavage structure assays (e.g. the INVADER assay) to screen nucleic acid samples, e.g., from patients, for the presence of mutations in the connexin 26 (Cx26) or gap-junction beta 2 gene (GJB2).

BACKGROUND OF THE INVENTION

Severe to profound congenital hearing loss affects approximately 1/1000 newborns in developed countries (Morton, in *The Genetics of Hearing Impairment*, The New York Acad. Sci., New York, 630, pp. 16-31 (1991) and Gorlin et al., *Hereditary hearing loss and its syndromes*, New York: Oxford University Press (1995)). At least half of all congenital hearing loss is due to inherited disorders, while the remaining cases are likely due to environmental factors such as acoustic trauma, ototoxic drug exposure, or bacterial or viral infection (ACMG, Genetics in Medicine, 4: 162-171 (2002)). Approximately 70% of inherited, congenital hearing loss is nonsyndromic (no additional symptoms present) (Steel and Kros, Nat. Genet. 27: 143-149 (2001)). Typically, nonsyndromic hearing impairment (NSHI) is attributable to sensorineural anomalies (ACMG, supra.).

Consistent with the complexity of the cochlear apparatus itself, which consists of over 1 million moving parts (Hudspeth, Science 230: 745-752 (1985)), over 77 loci associated with NSHI have been mapped to human chromosomes, and more than 50 of these have been sequenced (ACMG, supra.). These genes are subdivided based on their mode of inheritance. Deafness genes are named DFNA if autosomal dominant (22% of characterized loci), DFNB, if autosomal recessive (77% of characterized loci), or DFN if X-linked (1% of characterized loci) (ACMG, supra.). The majority of sensorineural NSHI appears to be monogenic (ACMG, supra.). Despite the diversity of associated loci, more than 50% of cases are due to autosomal recessive variations in a single gene, DFNB1, also known as connexin 26 (Cx26) and gap-junction beta 2 (GJB2) (reviewed in Kenneson, A. et al., Genetics in Medicine 4: 258-274 (2002)).

The connexin 26 protein was identified in 1989 in liver tissue (Zhang and Nicholson, J Cell Biol. 109: 3391-401 (1989)) and later associated with NSHI as DFNB1 (Guilford, et al., Nature Genet. 6: 24-8 (1994)). The gene is located on chromosome 13q11-12 (Mignon, C. et al., Cytogenet Cell Genet 72: 185-6 (1996)). Connexin 26 is a member of the connexin family of gap junction proteins, which are cellular channels that enable intercellular communication by spanning plasma membranes and linking the cytoplasm of adjacent cells (White, Brain Research Reviews 32: 181-183 (2000)). Each such channel is composed of two connexons, each of which in turn is an assembly of six connexin subunits. The connexin 26 protein is expressed in two groups of cochlear cells in the inner ear: non-sensory epithelial cells and connective tissue cells (Kelley et al., Am. J. Hum. Genet. 62: 792-799 (1998)). The majority of deafness-causing mutations of the connexin 26 gene are autosomal recessive, loss-of-function alleles that result in prematurely truncated protein. The loss of functional connexin 26 protein likely disrupts potassium ion flow within the cochlea, thus interfering with the normal functioning of hair cells and sensorineural function (reviewed in Lefebvre, Brain Research Reviews, 32: 159-162 (2000)).

Despite the identification of more than 90 variants in the connexin 26 protein, most of which result in amino acid changes, the majority of NSHI cases attributable to mutations in this gene result from just a handful of alleles, which in turn are population-based (Kenneson, A. supra.). A single base deletion of a G residue, alternately referred to as 30ΔG or 35ΔG, has a prevalence of 1-3% in Caucasian populations and accounts for ⅔ of cases of congenital deafness in these populations. By itself, this allele accounts for as much as 10% of all childhood hearing loss (Kelley et al., Brain Research Reviews, 32: 184-188 (2000) and Kelley, P. M. et al. Am. J. Hum. Genet. 62: 792-99 (1998)). This mutation results in the loss of one of six contiguous G residues in the upstream portion of the gene and results in prematurely truncated protein (White, Brain Research Reviews 32: 181-183 (2000)). This sequence appears to be a mutational hot spot and is similar to a sequence predicted to be a site of frequent DNA replication errors (Kelley, supra). Similarly, as many as 10% of Ashkenazi Jews carry a deletion of a T residue at 167 (167ΔT), while 1% of the Japanese and Korean populations carry 235ΔG. Preliminary studies suggest that penetrance of hearing loss in individuals homozygous for these alleles is complete in these populations (Kenneson, supra.).

A combination of factors, i.e. increased frequency of newborn hearing screening, improved accuracy of testing (Norton et al., Ear Hear, 21: 529-535 (2000)), and the demonstration that early detection of hearing loss coupled with intervention results in the development of language skills among pre-lingual deaf children that approach those of hearing children (Yoshinaga-Itano, et al., Pediatrics, 102: 1161-1171(1998) and Moeller, Pediatrics, 106: 3 e43 (2000)), has led to an increase in the use of genetic testing in follow-up analysis of infants with hearing loss as well as in the use of genetic counseling for families with hearing loss-affected offspring (ACMG, supra.). Molecular genetic methods applied to the analysis of connexin 26, or GJB2 mutations include the following (reviewed in Kenneson, supra): sequencing; allele-specific PCR, often followed by sequencing of positives; PCR-RFLP; PCR-SSCP of exons 1 and 2; PCR-DGGE; PCR with allele-specific probe hybridization; heteroduplex analysis followed by sequencing of positives. The majority of these methods, including methods described in U.S. Pat. Nos. 5,998,147 and 6,485,908 rely on PCR, and many require gel electrophoresis to discriminate the presence of variants. Moreover, with the exception of those approaches that involve sequencing, these methods do not distinguish between true heterozygotes and compound heterozygotes, i.e. individuals carrying two different variant alleles.

Given the potential importance of analysis of the connexin 26 and GJB2 genes in broad-based genetic testing for NSHI, there is a need for detection assays that may be applied directly to the analysis of connexin 26 and GJB2 sequences (e.g. genomic sequences), as well as assays that can be used to analyze large numbers of samples, i.e. high-throughput assays.

SUMMARY OF THE INVENTION

The present invention provides compositions and methods for the detection and characterization of mutations associated with congenital NSHI. More particularly, the present invention provides compositions, methods and kits for using invasive cleavage structure assays (e.g. the INVADER assay) to analyze nucleic acid samples, e.g., from patients, for the presence of two prevalent mutations in the connexin 26 gene associated with NSHI.

The method is not limited by the nature of the target nucleic acid. In some embodiments, the target nucleic acid comprises genomic DNA or mRNA. In some embodiments, the target nucleic acid is single stranded or double stranded DNA or RNA. In some embodiments, double stranded nucleic acid is rendered single stranded (e.g., by heat) prior to formation of the cleavage structure. In some embodiments, the source of target nucleic acid comprises a sample containing genomic DNA. Samples include, but are not limited to, blood, saliva, cerebral spinal fluid, pleural fluid, milk, lymph, sputum and semen.

In some embodiments, the present invention provides kits or compositions comprising a non-amplified oligonucleotide detection assay configured for detecting at least the 30ΔG (also referred to as the 35ΔG) or the 167ΔT allele. In other embodiments, the non-amplified oligonucleotide detection assay comprises first and second oligonucleotides configured to form an invasive cleavage structure (e.g. an INVADER assay) in combination with a target sequence comprising said at least one connexin 26 allele. In particular embodiments, the first oligonucleotide comprises a 5' portion and a 3' portion, wherein the 3' portion is configured to hybridize to the target sequence, and wherein the 5' portion is configured to not hybridize to the target sequence. In other embodiments, the second oligonucleotide comprises a 5' portion and a 3' portion, wherein the 5' portion is configured to hybridize to the target sequence, and wherein the 3' portion is configured to not hybridize to the target sequence.

In some embodiments, the at least one connexin 26 allele is 30ΔG or the wild-type version thereof. In other embodiments, the at least one connexin 26 allele is 167ΔT.

In some embodiments, the present invention provides methods of detecting an allele in the connexin 26 gene or method for diagnosing congenital NSHI (or carrier status), comprising; a) providing; i) a sample from a subject; and ii) a composition comprising an oligonucleotide detection assay (e.g. as described herein); and b) contacting said sample with said composition such that the presence or absence of at least one allele in said connexin 26 gene is determined. In some embodiments, the sample is a blood sample, mouth swab sample, saliva sample, or other biological fluid sample from the subject.

For example, in some embodiments, the present invention provides a kit comprising a non-amplified oligonucleotide detection assay configured for detecting at least one Connexin 26 allele. In some embodiments, the non-amplified oligonucleotide detection assay comprises first and second oligonucleotides configured to form an invasive cleavage structure in combination with a target sequence comprising the at least one Connexin 26 allele. In some embodiments, the first oligonucleotide comprises a 5' portion and a 3' portion, wherein the 3' portion is configured to hybridize to the target sequence, and wherein the 5' portion is configured to not hybridize to the target sequence. In some embodiments, the second oligonucleotide comprises a 5' portion and a 3' portion, wherein the 5' portion is configured to hybridize to the target sequence, and wherein the 3' portion is configured to not hybridize to the target sequence. In certain embodiments, at least one Connexin 26 allele is selected from the group consisting of 30ΔG or 167ΔT or the wild-type versions thereof. In some embodiments, the non-amplified oligonucleotide detection assay comprises a cleavage agent. In some embodiments, wherein the cleavage agent comprises a structure-specific nuclease. In some embodiments, the agent comprises a 5' nuclease. In some embodiments, the 5' nuclease comprises a FEN-1 endonuclease. In other embodiments, the 5' nuclease comprises a polymerase. In some embodiments, the kit further comprises instructions for using the kit for the detecting at least one connexin allele. In some embodiments, the instructions comprise instructions required by the United States Food and Drug Administration for labeling of analyte specific reagents, while in other embodiments, the instructions comprise instructions required by the United States Food and Drug Administration for labeling of in vitro diagnostics.

The present invention also provides a method for detecting at least one connexin 26 allele, comprising providing a sample comprising at least one connexin 26 allele; oligonucleotides configured to hybridize to the connexin 26 allele to form an invasive cleavage structure; and an agent that detects the presence of an invasive cleavage structure; and exposing the sample to the oligonucleotides and the agent. In some embodiments, the at least one Connexin 26 allele is selected from the group consisting of 30ΔG or 167ΔT or the wild-type versions thereof. In some embodiments, exposing the sample to the oligonucleotides and the agent comprises exposing the sample to the oligonucleotides and the agent under conditions wherein an invasive cleavage structure is formed between the at least one connexin allele and the oligonucleotides. In some embodiments, the method further comprises the step of detecting the invasive cleavage structure. In some embodiments, the agent comprises a cleavage agent, for example, a structure-specific nuclease. In other embodiments, the agent comprises a 5' nuclease. In some embodiments, the 5' nuclease comprises a FEN-1 endonuclease. In other embodiments, the 5' nuclease comprises a polymerase. In some embodiments, the oligonucleotides comprise first and second oligonucleotides, the first oligonucleotide comprising a portion complementary to a first region of the connexin 26 allele nucleic acid and the second oligonucleotide comprising a 3' portion and a 5' portion, the 5' portion complementary to a second region of the target nucleic acid downstream of and contiguous to the first portion of the connexin 26 allele.

The present invention further provides a kit comprising an oligonucleotide detection assay configured for detecting at least one Connexin 26 allele, wherein the kit comprises at least two oligonucleotides, and wherein two of the at least two oligonucleotides hybridize to both wild type and mutant connexin 26 alleles. In some embodiments, the at least one Connexin 26 allele is selected from the group including, but not limited to, 30ΔG or 167ΔT or the wild-type versions thereof. In some embodiments, the oligonucleotide detection assays comprise first and second oligonucleotides configured to form an invasive cleavage structure in combination with target sequences comprising the Connexin 26 alleles. In some embodiments, the first oligonucleotide comprises a 5' portion and a 3' portion, wherein the 3' portion is configured to hybridize to the target sequence, and wherein the 5' portion is configured to not hybridize to the target sequence. In some embodiments, the second oligonucleotide comprises a 5' portion and a 3' portion, wherein the 5' portion is configured to hybridize to the target sequence, and wherein the 3' portion is configured not to hybridize to the target sequence. In some embodiments, the oligonucleotide detection assays are selected from sequencing assays, polymerase chain reaction assays, hybridization assays, hybridization assays employing a probe complementary to a mutation, microarray assays, bead array assays, primer extension assays, enzyme mismatch cleavage assays, branched hybridization assays, rolling circle replication assays, NASBA assays, molecular beacon assays, cycling probe assays, ligase chain reaction assays, invasive cleavage structure assays, ARMS assays, and sandwich hybridization assays.

DEFINITIONS

To facilitate an understanding of the present invention, a number of terms and phrases are defined below:

As used herein, the terms "subject" and "patient" refer to any organisms including plants, microorganisms and animals (e.g., mammals such as dogs, cats, livestock, and humans).

As used herein, the term "INVADER assay reagents" refers to one or more reagents for detecting target sequences, said reagents comprising oligonucleotides capable of forming an invasive cleavage structure in the presence of the target sequence. In some embodiments, the INVADER assay reagents further comprise an agent for detecting the presence of an invasive cleavage structure (e.g., a cleavage agent). In some embodiments, the oligonucleotides comprise first and second oligonucleotides, said first oligonucleotide comprising a 5' portion complementary to a first region of the target nucleic acid and said second oligonucleotide comprising a 3' portion and a 5' portion, said 5' portion complementary to a second region of the target nucleic acid downstream of and contiguous to the first portion. In some embodiments, the 3' portion of the second oligonucleotide comprises a 3' terminal nucleotide not complementary to the target nucleic acid. In preferred embodiments, the 3' portion of the second oligonucleotide consists of a single nucleotide not complementary to the target nucleic acid.

In some embodiments, INVADER assay reagents are configured to detect a target nucleic acid sequence comprising first and second non-contiguous single-stranded regions separated by an intervening region comprising a double-stranded region. In preferred embodiments, the INVADER assay reagents comprise a bridging oligonucleotide capable of binding to the first and second non-contiguous single-stranded regions of a target nucleic acid sequence. In particularly preferred embodiments, either or both of the first or second oligonucleotides of the INVADER assay reagents are bridging oligonucleotides.

In some embodiments, the INVADER assay reagents further comprise a solid support. For example, in some embodiments, the one or more oligonucleotides of the assay reagents (e.g., first and/or second oligonucleotide, whether bridging or non-bridging) is attached to said solid support. In some embodiments, the INVADER assay reagents further comprise a buffer solution. In some preferred embodiments, the buffer solution comprises a source of divalent cations (e.g., $Mn^{2+}$ and/or $Mg^{2+}$ ions). Individual ingredients (e.g., oligonucleotides, enzymes, buffers, target nucleic acids) that collectively make up INVADER assay reagents are termed "INVADER assay reagent components".

In some embodiments, the INVADER assay reagents further comprise a third oligonucleotide complementary to a third portion of the target nucleic acid upstream of the first portion of the first target nucleic acid. In yet other embodiments, the INVADER assay reagents further comprise a target nucleic acid. In some embodiments, the INVADER assay reagents further comprise a second target nucleic acid. In yet other embodiments, the INVADER assay reagents further comprise a third oligonucleotide comprising a 5' portion complementary to a first region of the second target nucleic acid. In some specific embodiments, the 3' portion of the third oligonucleotide is covalently linked to the second target nucleic acid. In other specific embodiments, the second target nucleic acid further comprises a 5' portion, wherein the 5' portion of the second target nucleic acid is the third oligonucleotide. In still other embodiments, the INVADER assay reagents further comprise an ARRESTOR molecule (e.g., ARRESTOR oligonucleotide).

In some preferred embodiments, the INVADER assay reagents further comprise reagents for detecting a nucleic acid cleavage product. In some embodiments, one or more oligonucleotides in the INVADER assay reagents comprise a label. In some preferred embodiments, the first oligonucleotide comprises a label. In other preferred embodiments, the third oligonucleotide comprises a label. In particularly preferred embodiments, the reagents comprise a first and/or a third oligonucleotide labeled with moieties that produce a fluorescence resonance energy transfer (FRET) effect.

In some embodiments one or more the INVADER assay reagents may be provided in a predispensed format (i.e., premeasured for use in a step of the procedure without re-measurement or re-dispensing). In some embodiments, selected INVADER assay reagent components are mixed and predispensed together. In other embodiments, In preferred embodiments, predispensed assay reagent components are predispensed and are provided in a reaction vessel (including but not limited to a reaction tube or a well, as in, e.g., a microtiter plate). In particularly preferred embodiments, predispensed INVADER assay reagent components are dried down (e.g., desiccated or lyophilized) in a reaction vessel.

In some embodiments, the INVADER assay reagents are provided as a kit. As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

In some embodiments, the present invention provides INVADER assay reagent kits comprising one or more of the components necessary for practicing the present invention. For example, the present invention provides kits for storing or delivering the enzymes and/or the reaction components necessary to practice an INVADER assay. The kit may include any and all components necessary or desired for assays including, but not limited to, the reagents themselves, buffers, control reagents (e.g., tissue samples, positive and negative control target oligonucleotides, etc.), solid supports, labels, written and/or pictorial instructions and product information, inhibitors, labeling and/or detection reagents, package environmental controls (e.g., ice, desiccants, etc.), and the like. In some embodiments, the kits provide a sub-set of the required components, wherein it is expected that the user will supply the remaining components. In some embodiments, the kits comprise two or more separate containers wherein each container houses a subset of the components to be delivered. For example, a first container (e.g., box) may contain an enzyme (e.g., structure specific cleavage enzyme in a suitable storage buffer and container), while a second box may contain oligonucleotides (e.g., INVADER oligonucleotides, probe oligonucleotides, control target oligonucleotides, etc.).

The term "label" as used herein refers to any atom or molecule that can be used to provide a detectable (preferably quantifiable) effect, and that can be attached to a nucleic acid or protein. Labels include but are not limited to dyes such as fluorescein, CASCADE BLUE, hexachloro-fluorescein, tetrachloro-fluorescein, TAMRA, ROX, VIC, JOE, Cy3, Cy3.5, Cy5, Cy5.5, 4,4-difluoro-5,7-diphenyl-4-bora-3a,4a-diaza-s-indacene-3-propionic acid, 4,4-difluoro-5,p-methoxyphenyl-4-bora-3a,4a-diaza-s-indacene-3-propionic acid, 4,4-difluoro-5-styryl-4-bora-3a,4-adiaz-a-S-indacene-propionic acid, 6-carboxy-X-rhodamine, N,N,N',N'-tetramethyl-6-carboxyrhodamine, TEXAS RED, eosin, 4,4-difluoro-5,7-diphenyl-4-bora-3a,4a-diaza-s-indacene-3-propionic acid, 4,4-difluoro-5,p-ethoxyphenyl-4-bora-3a,4a-diaza-s-indacene 3-propionic acid and 4,4-difluoro-5-styryl-4-bora-3a,4a-diaza-S-indacene-propionic acid, BOTHEL BLUE, REDMOND RED, YAKIMA YELLOW; radiolabels such as 32P; binding moieties such as biotin and minor groove binders (MGBs) such as distamycin and CC-1065 (Epoch Biosciences, Redmond Wash.); haptens such as digoxgenin; luminogenic, phosphorescent or fluorogenic moieties; and fluorescent dyes alone or in combination with moieties that can suppress or shift emission spectra by fluorescence resonance energy transfer (FRET). Labels comprise moieties that quench fluorescence or other energy emissions, ("quenchers"), including but not limited to dabcyl, QSY7 (Molecular Probes, Eugene, Oreg.), and ECLIPSE quenchers (Synthetic Genetics, San Diego, Calif.). Labels may provide signals detectable by any means, including but not limited to, fluorescence, radioactivity, colorimetry, gravimetry, X-ray diffraction or absorption, magnetism, effects of mass (e.g., rotation, time-of-flight, etc), enzymatic activity, and the like. A label may be detected in any fashion, including but not limited to, by use of the unaided senses (e.g., by smell, sound, visual effect, etc.), by an instrument (e.g. a camera, fluorimeter, charge-coupled device, scintillation counter, polarimeter, spectrometer, etc.) or a reactive medium (X-ray or camera film, pH indicator, etc.), that can convey to a user or to another component of a system (e.g., a computer or controller) the presence of a signal or effect. Such detection may comprise detection of ultraviolet, visible or infrared light, including fluorescence or chemiluminescence; a radiation; a spectroscopic effect such as nuclear magnetic resonance, mass (e.g., by spectrometry) or surface enhanced Raman effects or plasmon resonance. A label may be a charged moiety (positive or negative charge) or alternatively, may be charge neutral. Labels can include or consist of a nucleic acid or protein sequence, so long as the sequence is detectable.

As used herein, the term "distinct" in reference to signals refers to signals that can be differentiated one from another, e.g., by spectral properties such as fluorescence emission wavelength, color, absorbance, mass, size, fluorescence polarization properties, charge, etc., or by capability of interaction with another moiety, such as with a chemical reagent, an enzyme, an antibody, etc.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand. Nucleotide analogs used to form non-standard base pairs, whether with another nucleotide analog (e.g., an IsoC/IsoG base pair), or with a naturally occurring nucleotide (e.g., as described in U.S. Pat. No. 5,912,340, herein incorporated by reference in its entirety) are also considered to be complementary to a base pairing partner within the meaning this definition. Further, when nucleotides are known to form pairs with multiple different bases, e.g., IsoG nucleotide ability to pair with IsoC and with T nucleotides, each of the bases with which it can form a hydrogen-bonded base-pair falls within the meaning of "complementary," as used herein. "Universal" bases, i.e., those that can form base pairs with several other bases, such as the "wobble" base inosine, are considered complementary to those bases with which pairs can be formed.

The term "homology" and "homologous" refers to a degree of identity. There may be partial homology or complete homology. A partially homologous sequence is one that is less than 100% identical to another sequence.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (see e.g., Anderson and Young, Quantitative Filter Hybridization, in Nucleic Acid Hybridization (1985). Other references (e.g., Allawi and SantaLucia, Biochemistry 36, 10581-94 (1997)) include more sophisticated computations that take structural and environmental, as well as sequence characteristics into account for the calculation of $T_m$.

The term "gene" refers to a DNA sequence that comprises control and coding sequences necessary for the production of an RNA having a non-coding function (e.g., a ribosomal or transfer RNA), a polypeptide or a precursor. The RNA or polypeptide can be encoded by a full length coding sequence or by any portion of the coding sequence so long as the desired activity or function is retained.

The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified", "mutant" or "polymorphic" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "recombinant DNA vector" as used herein refers to DNA sequences containing a desired heterologous sequence. For example, although the term is not limited to the use of expressed sequences or sequences that encode an expression product, in some embodiments, the heterologous sequence is a coding sequence and appropriate DNA sequences necessary for either the replication of the coding sequence in a host organism, or the expression of the operably linked coding sequence in a particular host organism. DNA sequences necessary for expression in prokaryotes include a promoter, optionally an operator sequence, a ribosome binding site and possibly other sequences. Eukaryotic cells are known to utilize promoters, polyadenlyation signals and enhancers.

The term "oligonucleotide" as used herein is defined as a molecule comprising two or more deoxyribonucleotides or ribonucleotides, preferably at least 5 nucleotides, more preferably at least about 10-15 nucleotides and more preferably at least about 15 to 30 nucleotides. The exact size will depend on many factors, which in turn depend on the ultimate function or use of the oligonucleotide. The oligonucleotide may be generated in any manner, including chemical synthesis, DNA replication, reverse transcription, PCR, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

The term "primer" refers to an oligonucleotide that is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The term "cleavage structure" as used herein, refers to a structure that is formed by the interaction of at least one probe oligonucleotide and a target nucleic acid, forming a structure comprising a duplex, the resulting structure being cleavable by a cleavage means, including but not limited to an enzyme. The cleavage structure is a substrate for specific cleavage by the cleavage means in contrast to a nucleic acid molecule that is a substrate for non-specific cleavage by agents such as phosphodiesterases, which cleave nucleic acid molecules without regard to secondary structure (i.e., no formation of a duplexed structure is required).

The term "cleavage means" or "cleavage agent" as used herein refers to any means that is capable of cleaving a cleavage structure, including but not limited to enzymes. "Structure-specific nucleases" or "structure-specific enzymes" are enzymes that recognize specific secondary structures in a nucleic molecule and cleave these structures. The cleavage means of the invention cleave a nucleic acid molecule in response to the formation of cleavage structures; it is not necessary that the cleavage means cleave the cleavage structure at any particular location within the cleavage structure.

The cleavage means may include nuclease activity provided from a variety of sources including the Cleavase enzymes, the FEN-1 endonucleases (including RAD2 and XPG proteins), Taq DNA polymerase and *E. coli* DNA polymerase I. The cleavage means may include enzymes having 5' nuclease activity (e.g., Taq DNA polymerase (DNAP), *E. coli*

DNA polymerase D). The cleavage means may also include modified DNA polymerases having 5' nuclease activity but lacking synthetic activity. Examples of cleavage means suitable for use in the method and kits of the present invention are provided in U.S. Pat. Nos. 5,614,402; 5,795,763; 5,843,669; 6,090,606; U.S., patent application Ser. No. 09/577,304; PCT Appln. Nos WO 98/23774; WO 02/070755A2; WO0190337A2; WO03073067A2, each of which is herein incorporated by reference it its entirety.

The term "thermostable" when used in reference to an enzyme, such as a 5' nuclease, indicates that the enzyme is functional or active (i.e., can perform catalysis) at an elevated temperature, i.e., at about 55° C. or higher.

The term "cleavage products" as used herein, refers to products generated by the reaction of a cleavage means with a cleavage structure (i.e., the treatment of a cleavage structure with a cleavage means).

The term "target nucleic acid" refers to a nucleic acid molecule containing a sequence that has at least partial complementarity with at least a probe oligonucleotide and may also have at least partial complementarity with an INVADER oligonucleotide. The target nucleic acid may comprise single- or double-stranded DNA or RNA.

The term "non-target cleavage product" refers to a product of a cleavage reaction that is not derived from the target nucleic acid. As discussed above, in the methods of the present invention, cleavage of the cleavage structure generally occurs within the probe oligonucleotide. The fragments of the probe oligonucleotide generated by this target nucleic acid-dependent cleavage are "non-target cleavage products."

The term "probe oligonucleotide" refers to an oligonucleotide that interacts with a target nucleic acid to form a cleavage structure in the presence or absence of an INVADER oligonucleotide. When annealed to the target nucleic acid, the probe oligonucleotide and target form a cleavage structure and cleavage occurs within the probe oligonucleotide.

The term "INVADER oligonucleotide" refers to an oligonucleotide that hybridizes to a target nucleic acid at a location near the region of hybridization between a probe and the target nucleic acid, wherein the INVADER oligonucleotide comprises a portion (e.g., a chemical moiety, or nucleotide-whether complementary to that target or not) that overlaps with the region of hybridization between the probe and target. In some embodiments, the INVADER oligonucleotide contains sequences at its 3' end that are substantially the same as sequences located at the 5' end of a probe oligonucleotide.

The term "cassette" as used herein refers to an oligonucleotide or combination of oligonucleotides configured to generate a detectable signal in response to cleavage of a probe oligonucleotide in an INVADER assay. In preferred embodiments, the cassette hybridizes to a non-target cleavage product from cleavage of the probe oligonucleotide to form a second invasive cleavage structure, such that the cassette can then be cleaved.

In some embodiments, the cassette is a single oligonucleotide comprising a hairpin portion (i.e., a region wherein one portion of the cassette oligonucleotide hybridizes to a second portion of the same oligonucleotide under reaction conditions, to form a duplex). In other embodiments, a cassette comprises at least two oligonucleotides comprising complementary portions that can form a duplex under reaction conditions. In preferred embodiments, the cassette comprises a label. In particularly preferred embodiments, cassette comprises labeled moieties that produce a fluorescence resonance energy transfer (FRET) effect.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

As used herein, the phrase "non-amplified oligonucleotide detection assay" refers to a detection assay configured to detect the presence or absence of a particular polymorphism (e.g., SNP, repeat sequence, etc.) in a target sequence (e.g. genomic DNA) that has not been amplified (e.g. by PCR), without creating copies of the target sequence. A "non-amplified oligonucloetide detection assay" may, for example, amplify a signal used to indicate the presence or absence of a particular polymorphism in a target sequence, so long as the target sequence is not copied.

As used herein, the phrase "non-amplifying oligonucleotide detection assay" refers to a detection assay configured to detect the presence or absence of a particular polymorphism (e.g., SNP, repeat sequence, etc.) in a target sequence (e.g., genomic DNA, or amplified or other synthetic DNA), without creating copies of the target sequence. A "non-amplifying oligonucleotide detection assay" may, for example, amplify a signal used to indicate the presence or absence of a particular polymorphism in a target sequence, so long as the target sequence is not copied.

The term "sequence variation" as used herein refers to differences in nucleic acid sequence between two nucleic acids. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

The term "liberating" as used herein refers to the release of a nucleic acid fragment from a larger nucleic acid fragment, such as an oligonucleotide, by the action of, for example, a 5' nuclease such that the released fragment is no longer covalently attached to the remainder of the oligonucleotide.

The term "$K_m$" as used herein refers to the Michaelis-Menten constant for an enzyme and is defined as the concentration of the specific substrate at which a given enzyme yields one-half its maximum velocity in an enzyme catalyzed reaction.

The term "nucleotide analog" as used herein refers to modified or non-naturally occurring nucleotides including, but not limited to, analogs that have altered stacking interactions such as 7-deaza purines (i.e., 7-deaza-dATP and 7-deaza-dGTP); base analogs with alternative hydrogen bonding configurations (e.g., such as Iso-C and Iso-G and other non-standard base pairs described in U.S. Pat. No. 6,001,983 to S. Benner); non-hydrogen bonding analogs (e.g., non-polar, aromatic nucleoside analogs such as 2,4-difluorotoluene, described by Schweitzer and Kool, J. Org. Chem., 1994, 59, 7238-7242, Schweitzer and Kool, J. Am. Chem. Soc., 1995, 117, 1863-1872); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152). The term also comprises other known base analogs of DNA and RNA bases, including, but not limited to, 4-acetylcytosine, 8-hydroxy-N6-methyladenosine, aziridinylcytosine, pseudo-isocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. Nucleotide analogs comprise modified forms of deoxyribonucleotides as well as ribonucleotides.

The term "polymorphic locus" is a locus present in a population that shows variation between members of the population (e.g., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "microorganism" as used herein means an organism too small to be observed with the unaided eye and includes, but is not limited to bacteria, virus, protozoans, fungi, and ciliates.

The term "microbial gene sequences" refers to gene sequences derived from a microorganism.

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery).

The term "multi-drug resistant" or multiple-drug resistant" refers to a microorganism that is resistant to more than one of the antibiotics or antimicrobial agents used in the treatment of said microorganism.

The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The term "source of target nucleic acid" refers to any sample that contains nucleic acids (RNA or DNA). Particularly preferred sources of target nucleic acids are biological samples including, but not limited to blood, saliva, cerebral spinal fluid, pleural fluid, milk, lymph, sputum and semen.

An oligonucleotide is said to be present in "excess" relative to another oligonucleotide (or target nucleic acid sequence) if that oligonucleotide is present at a higher molar concentration that the other oligonucleotide (or target nucleic acid sequence). When an oligonucleotide such as a probe oligonucleotide is present in a cleavage reaction in excess relative to the concentration of the complementary target nucleic acid sequence, the reaction may be used to indicate the amount of the target nucleic acid present. Typically, when present in excess, the probe oligonucleotide will be present at least a 100-fold molar excess; typically at least 1 pmole of each probe oligonucleotide would be used when the target nucleic acid sequence was present at about 10 fmoles or less.

A sample "suspected of containing" a first and a second target nucleic acid may contain either, both or neither target nucleic acid molecule.

The term "reactant" is used herein in its broadest sense. The reactant can comprise, for example, an enzymatic reactant, a chemical reactant or light (e.g., ultraviolet light, particularly short wavelength ultraviolet light is known to break oligonucleotide chains). Any agent capable of reacting with an oligonucleotide to either shorten (e.g., cleave) or elongate the oligonucleotide is encompassed within the term "reactant."

As used herein, the term "purified" or "to purify" refers to the removal of contaminants from a sample. For example, recombinant CLEAVASE nucleases are expressed in bacterial host cells and the nucleases are purified by the removal of host cell proteins; the percent of these recombinant nucleases is thereby increased in the sample.

As used herein the term "portion" when in reference to a protein (as in "a portion of a given protein") refers to fragments of that protein. The fragments may range in size from four amino acid residues to the entire amino acid sequence minus one amino acid (e.g., 4, 5, 6, . . . , n−1).

The term "nucleic acid sequence" as used herein refers to an oligonucleotide, nucleotide or polynucleotide, and fragments or portions thereof, and to DNA or RNA of genomic or synthetic origin that may be single or double stranded, and represent the sense or antisense strand. Similarly, "amino acid sequence" as used herein refers to peptide or protein sequence.

As used herein, the terms "purified" or "substantially purified" refer to molecules, either nucleic or amino acid sequences, that are removed from their natural environment, isolated or separated, and are at least 60% free, preferably 75% free, and most preferably 90% free from other components with which they are naturally associated. An "isolated polynucleotide" or "isolated oligonucleotide" is therefore a substantially purified polynucleotide.

The term "continuous strand of nucleic acid" as used herein is means a strand of nucleic acid that has a continuous, covalently linked, backbone structure, without nicks or other disruptions. The disposition of the base portion of each nucleotide, whether base-paired, single-stranded or mismatched, is not an element in the definition of a continuous strand. The backbone of the continuous strand is not limited to the ribose-phosphate or deoxyribose-phosphate compositions that are found in naturally occurring, unmodified nucleic acids. A nucleic acid of the present invention may comprise modifications in the structure of the backbone, including but not limited to phosphorothioate residues, phosphonate residues, 2' substituted ribose residues (e.g., 2'-O-methyl ribose) and alternative sugar (e.g., arabinose) containing residues.

The term "continuous duplex" as used herein refers to a region of double stranded nucleic acid in which there is no disruption in the progression of basepairs within the duplex (i.e., the base pairs along the duplex are not distorted to accommodate a gap, bulge or mismatch with the confines of the region of continuous duplex). As used herein the term refers only to the arrangement of the basepairs within the duplex, without implication of continuity in the backbone portion of the nucleic acid strand. Duplex nucleic acids with uninterrupted basepairing, but with nicks in one or both strands are within the definition of a continuous duplex.

The term "duplex" refers to the state of nucleic acids in which the base portions of the nucleotides on one strand are bound through hydrogen bonding to their complementary bases arrayed on a second strand. The condition of being in a duplex form reflects on the state of the bases of a nucleic acid. By virtue of base pairing, the strands of nucleic acid also generally assume the tertiary structure of a double helix, having a major and a minor groove. The assumption of the helical form is implicit in the act of becoming duplexed.

The term "template" refers to a strand of nucleic acid on which a complementary copy is built from nucleoside triphosphates through the activity of a template-dependent nucleic acid polymerase. Within a duplex the template strand is, by convention, depicted and described as the "bottom" strand. Similarly, the non-template strand is often depicted and described as the "top" strand.

DESCRIPTION OF THE DRAWINGS

FIG. 4 shows an exemplary cleavage structure of the present invention, designed for detection of the del35G mutation of connexin 26.

DESCRIPTION OF THE INVENTION

The present invention provides means for forming a nucleic acid cleavage structure that is dependent upon the presence of a target nucleic acid and cleaving the nucleic acid cleavage structure so as to release distinctive cleavage products. 5' nuclease activity, for example, is used to cleave the target-dependent cleavage structure and the resulting cleavage products are indicative of the presence of specific target nucleic acid sequences in the sample. When two strands of nucleic acid, or oligonucleotides, both hybridize to a target nucleic acid strand such that they form an overlapping invasive cleavage structure, as described below, invasive cleavage can occur. Through the interaction of a cleavage agent (e.g., a 5' nuclease) and the upstream oligonucleotide, the cleavage agent can be made to cleave the downstream oligonucleotide at an internal site in such a way that a distinctive fragment is produced. Such embodiments have been termed the INVADER assay (Third Wave Technologies) and are described in U.S. Pat. Nos. 5,846,717; 6,001,567; 5,985,557; 5,994,069; 6,090,543; 6,348,314; 6,458,535; U.S. patent application Nos. 20030186238 (Ser. No. 10/084839); 20030104378A1 (Ser. No. 09/864636); Lyamichev et al., Nat. Biotech., 17:292 (1999), Hall et al., PNAS, USA, 97:8272 (2000), WO97/27214 and WO98/42873, each of which is herein incorporated by reference in their entirety for all purposes).

The INVADER assay detects hybridization of probes to a target by enzymatic cleavage of specific structures by structure specific enzymes (See, INVADER assays, Third Wave Technologies; See e.g., U.S. Pat. Nos. 5,614,402; 5,795,763; 5,843,669; 6,090,606; U.S., patent application Ser. No. 09/577,304; PCT Appln. Nos WO 98/23774; WO 02/070755A2; WO0190337A2, WO03073067A2, each of which is herein incorporated by reference it its entirety, each of which is herein incorporated by reference in its entirety for all purposes).

Figure 1:
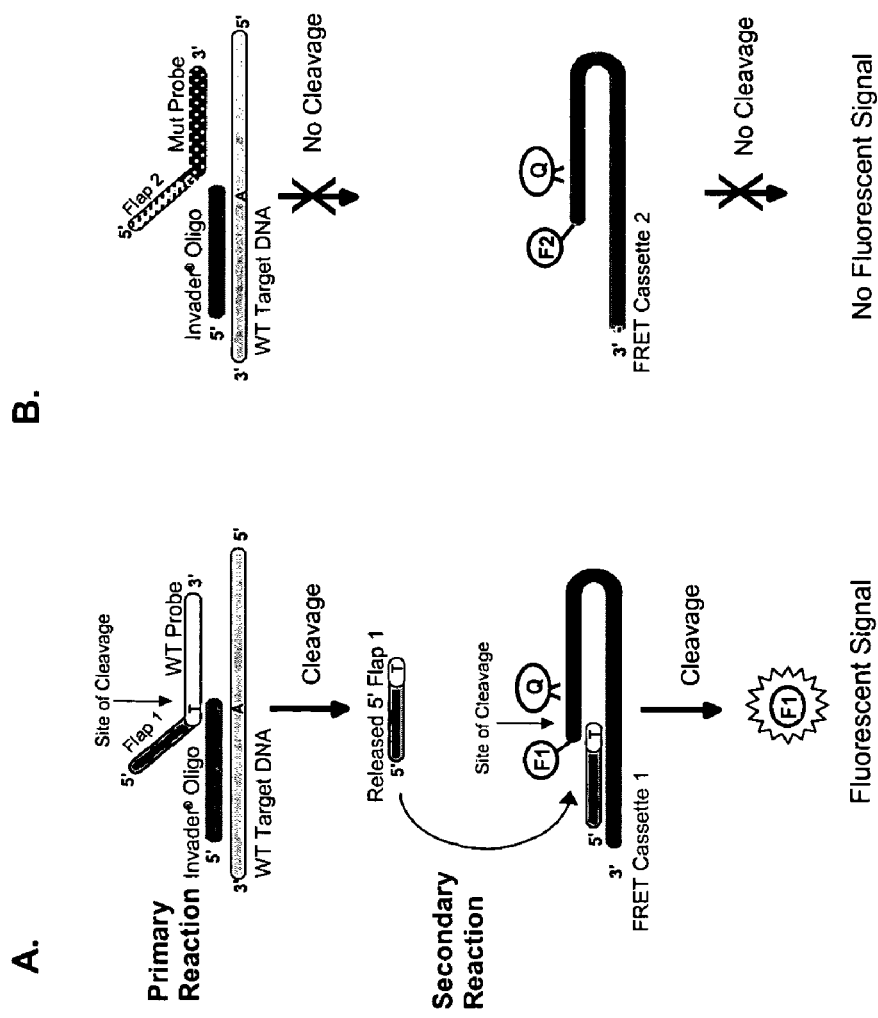
FIG. 1 shows a schematic diagram of INVADER oligonucleotides, probe oligonucleotides and FRET cassettes for detecting a two different alleles (e.g., differing by a single nucleotide) in a single reaction.

The INVADER assay detects specific DNA and RNA sequences by using structure-specific enzymes (e.g. FEN endonucleases) to cleave a complex formed by the hybridization of overlapping oligonucleotide probes (See, e.g. FIG. 1). Elevated temperature and an excess of one of the probes enable multiple probes to be cleaved for each target sequence present without temperature cycling. In some embodiments, these cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

Other modifications may be employed to alter other aspects of oligonucleotide performance in an assay. For example, the use of base analogs or modified bases can alter enzyme recognition of the oligonucleotide. Such modifications may comprise modifications to any portion or portions of a nucleotide, including but not limited to a base moiety, a sugar moiety or a phosphate group, and may comprise addition of, deletion of, and/or substitution of on or more atoms or groups of atoms (e.g., side or R groups) of the nucleotide. In some embodiments, such modifications are used to protect a region of an oligonucleotide from nuclease cleavage. In other embodiments, such modifications are used to alter the interaction between an enzyme and a nucleic acid structure comprising the modification (e.g., alter the binding to, or activity on the structure by the enzyme).

In some embodiments, modifications are used to affect the ability of an oligonucleotide to participate as a member of a cleavage structure that is not in a position to be cleaved (e.g., to serve as an INVADER oligonucleotide to enable cleavage of a probe). Such modifications may be referred to as "blocker" or "blocking" modifications. In some embodiments, assay oligonucleotides incorporate 2'-O-methyl modifications. In other embodiments, assay oligonucleotides incorporate 3' terminal modifications (e.g., $NH_2$; 3' hexanol; 3' hexanediol; 3' phosphate; 3' biotin; PMC, i.e. 3-(P-methoxyphenyl) 1,2 propanediol). In some embodiments, the blocking modifications are aliphatic linear hydrocarbons, e.g. $C_{12}$, $C_{14}$, or $C_{16}$ linkers. While any modification that can be attached to the 3' terminus of an oligonucleotide, either directly during synthesis or post-synthetically, may be contemplated for use as a blocker, some modifications may be less suitable based on their effects on INVADER assay performance. The suitability of a given 3' terminal oligonucleotide modification may be evaluated by (a) synthesizing the oligonucleotide;
(b) incorporating the modification;
(c) using the modified oligonucleotide in as a probe oligonucleotide in a standard INVADER assay on all of the following:
  (i) a complementary target
  (ii) a largely complementary target that contains a polymorphism at the nucleotide corresponding to position 1 in the probe oligonucleotide
  (iii) no target
(d) comparing signal generated in (c) to that generated in a standard INVADER assay on i-iii in which the probe oligonucleotide contains one of the following terminal modifications: e.g., $NH_2$; 3' hexanol; 3' hexanediol; 3' phosphate; 3' biotin; PMC, i.e. 3-(P-methoxyphenyl) 1,2 propanediol. Comparison of the signals generated using the candidate blocker modification to the established blocker modification will reveal whether the candidate results in more background signal generation and/or reduced target-dependent signal generation in an INVADER assay. Depending on the extent to which background and/or target-dependent signal is affected by the modification, it may be judged to be better than, equivalent to, or worse than other modifications suitable for use as blockers.

The INVADER assay detects specific mutations and SNPs in unamplified, as well as amplified, RNA and DNA including genomic DNA. In the embodiments shown schematically in FIG. 1, the INVADER assay uses two cascading steps (a primary and a secondary reaction) both to generate and then to amplify the target-specific signal. For convenience, the alleles in the following discussion are described as wild-type (WT) and mutant (MT), even though this terminology does not apply to all genetic variations. In the primary reaction (FIG. 1, panel A), the WT primary probe and the INVADER oligonucleotide hybridize in tandem to the target nucleic acid to form an overlapping structure. An unpaired "flap" is included on the 5' end of the WT primary probe. A structure-specific enzyme (e.g. the CLEAVASE enzyme, Third Wave Technologies) recognizes the overlap and cleaves off the unpaired flap, releasing it as a target-specific product. In the secondary reaction, this cleaved product serves as an INVADER oligonucleotide on the WT fluorescence resonance energy transfer (WT-FRET) probe to again create the structure recognized by the structure specific enzyme (panel A). When the two dyes on a single FRET probe are separated by cleavage (indicated by the arrow in FIG. 1), a detectable fluorescent signal above background fluorescence is produced. Consequently, cleavage of this second structure results in an increase in fluorescence, indicating the presence of the WT allele (or mutant allele if the assay is configured for the mutant allele to generate the detectable signal). In some embodiments, FRET probes having different labels (e.g. resolvable by difference in emission or excitation wavelengths, or resolvable by time-resolved fluorescence detection) are provided for each allele or locus to be detected, such that the different alleles or loci can be detected in a single reaction. In such embodiments, the primary probe sets and the different FRET probes may be combined in a single assay, allowing comparison of the signals from each allele or locus in the same sample.

If the primary probe oligonucleotide and the target nucleotide sequence do not match at the cleavage site (e.g., as with the MT primary probe and the WT target, FIG. 1, panel B), the overlapped structure does not form and cleavage is suppressed. The structure specific enzyme (e.g., CLEAVASE VIII enzyme, Third Wave Technologies) used cleaves the overlapped structure more efficiently (e.g. at least 340-fold) than the non-overlapping structure, allowing excellent discrimination of the alleles.

The probes turn over without temperature cycling to produce many signals per target (i.e., linear signal amplification). Similarly, each target-specific product can enable the cleavage of many FRET probes.

The primary INVADER assay reaction is directed against the target DNA (or RNA) being detected. The target DNA is the limiting component in the first invasive cleavage, since the INVADER and primary probe are supplied in molar excess. In the second invasive cleavage, it is the released flap that is limiting. When these two cleavage reactions are performed sequentially, the fluorescence signal from the composite reaction accumulates linearly with respect to the target DNA amount.

In certain embodiments, the INVADER assay, or other nucleotide detection assays, are performed with accessible site designed oligonucleotides and/or bridging oligonucleotides. Such methods, procedures and compositions are described in U.S. Pat. No. 6,194,149, WO9850403, and WO0198537, all of which are specifically incorporated by reference in their entireties.

In some embodiments, the target nucleic acid comprises genomic DNA. In some preferred embodiments, the exposing of the sample to the oligonucleotides and the agent comprises exposing the sample to the oligonucleotides and the agent under conditions wherein an invasive cleavage structure is formed between said target sequence and said oligonucleotides if said target sequence is present in said sample, wherein said invasive cleavage structure is cleaved by said cleavage agent to form a cleavage product.

In some particularly preferred embodiments, the target sequence comprises a first region and a second region, said second region downstream of and contiguous to said first region, and said oligonucleotides comprise first and second oligonucleotides, said wherein at least a portion of said first oligonucleotide is completely complementary to said first portion of said target sequence and wherein said second oligonucleotide comprises a 3' portion and a 5' portion, wherein said 5' portion is completely complementary to said second portion of said target nucleic acid.

In some preferred embodiments, the exposing of the sample to the oligonucleotides and the agent comprises exposing the sample to the oligonucleotides and the agent under conditions wherein an invasive cleavage structure is formed between said target sequence and said oligonucleotides if said target sequence is present in said sample, wherein said invasive cleavage structure is cleaved by said cleavage agent to form a cleavage product.

In some preferred embodiments, the exposing of the sample to the oligonucleotides and the agent comprises exposing the sample to the oligonucleotides and the agent under conditions wherein an invasive cleavage structure is formed between said target sequence and said oligonucleotides if said target sequence is present in said sample, wherein said invasive cleavage structure is cleaved by said cleavage agent to form a cleavage product.

In some particularly preferred embodiments, the target sequence comprises a first region and a second region, said second region downstream of and contiguous to said first region, and said oligonucleotides comprise first and second oligonucleotides, said wherein at least a portion of said first oligonucleotide is completely complementary to said first portion of said target sequence and wherein said second oligonucleotide comprises a 3' portion and a 5' portion, wherein said 5' portion is completely complementary to said second portion of said target nucleic acid.

The present invention further provides assays in which the target nucleic acid is reused or recycled during multiple rounds of hybridization with oligonucleotide probes and cleavage of the probes without the need to use temperature cycling (i.e., for periodic denaturation of target nucleic acid strands) or nucleic acid synthesis (i.e., for the polymerization-based displacement of target or probe nucleic acid strands). When a cleavage reaction is run under conditions in which the probes are continuously replaced on the target strand (e.g. through probe-probe displacement or through an equilibrium between probe/target association and disassociation, or through a combination comprising these mechanisms, (The kinetics of oligonucleotide replacement. Luis P. Reynaldo, Alexander V. Vologodskii, Bruce P. Neri and Victor I. Lyamichev. J. Mol. Biol. 97: 511-520 (2000)), multiple probes can hybridize to the same target, allowing multiple cleavages, and the generation of multiple cleavage products.

Using Secondary Reaction to Distinguish Alleles

In some embodiments, the INVADER assay is designed such that the oligonucleotides using in a primary INVADER assay reaction hybridize and are cleaved approximately equivalently whether or not the target sequence has the wild-type or mutant allele. In such embodiments, the nature of the cleavage products generated by the reaction can be designed to differ, such that a secondary reaction is able to distinguish the identity and nature of the target sequence. Such embodiments find use, for example, where the mutant is a deletion or insertion in a repeat sequence (e.g., GGGGGG vs GGGGG, AGAGAGAG vs. AGAGAG, etc.). One such embodiment is shown in FIG. 4, using Connexin 26 as an exemplary embodiment. The wild type (DM WT) and mutant (SNP4b Del) probe oligonucleotides hybridize to the target nucleic acid whether the target has a G deletion or has the wild-type sequence. In each case, the cleavage structure is cleaved. However, the released cleavage fragment differs depending on the nature of the target sequence and is or is not capable of forming a competent cleavage structure in the secondary reaction depending on which target is present in the sample. For example, in FIG. 4, the deletion mutant probe will form a cleavage fragment that terminates in two C's on the wild type sequence and three C's on the mutant sequence. Only the three C fragment forms a competent cleavage structure on the secondary target (SNP4b Red FRET with Fam stem).

Thus, generally, the present invention provides compositions and methods for detecting target sequences whereby the oligonucleotides that hybridize to the target sequence will bind to both wild type and mutant sequences (i.e., the hybridization event does not provide the discrimination power). Only through the unique cleavage structure specificity of the cleavage agents of the present invention is the discrimination achieved, whereby unique cleavage products are produced dependent on the nature of the target. The cleavage products are identified in a secondary reaction that does not directly utilize the target sequence.

The INVADER Assay Reaction

In some preferred embodiments, in the INVADER DNA Assay, two oligonucleotides (a discriminatory Primary Probe and an INVADER Oligo) hybridize in tandem to the target DNA to form an overlapping structure. The 5'-end of the Primary Probe includes a 5'-flap that does not hybridize to the target DNA (FIG. 1). The 3'-nucleotide of the bound INVADER oligonucleotide overlaps the Primary Probe, but need not hybridize to the target DNA. The CLEAVASE enzyme recognizes this overlapping structure and cleaves off the unpaired 5'-flap of the Primary Probe, releasing it as a target-specific product. The Primary Probe is designed to have a melting temperature close to the reaction temperature. Thus, under the isothermal assay conditions, Primary Probes, which are provided in excess, cycle on the target DNA. This allows for multiple rounds of Primary Probe cleavage for each target DNA, and amplification of the number of released 5'-flaps.

In the secondary reaction, each released 5'-flap can serve as an INVADER oligonucleotide on a fluorescence resonance energy transfer (FRET) Cassette to create another overlapping structure that is recognized and cleaved by the CLEAVASE enzyme (FIG. 1). When the FRET Cassette is cleaved, the fluorophore (F) and quencher (Q) are separated, generating detectable fluorescence signal. Similar to the initial reaction, the released 5'-flap and the FRET Cassette cycle, resulting in amplified fluorescence signal. The initial and secondary reactions run concurrently in the same well.

The biplex format of the INVADER DNA Assay enables simultaneous detection of two DNA sequences in a single well. Most often, this involves detection of two variants of a particular polymorphism. The biplex format uses two different discriminatory Primary Probes, each with a unique 5'-flap, and two different FRET Cassettes, each with a spectrally distinct fluorophore. By design, the released 5'-flaps will bind only to their respective FRET Cassettes to generate a target-specific signal.

In some embodiments, the present invention provides kits comprising one or more of the components necessary for practicing the present invention. For example, the present invention provides kits for storing or delivering the enzymes of the present invention and/or the reaction components necessary to practice a cleavage assay (e.g., the INVADER assay). By way of example, and not intending to limit the kits of the present invention to any particular configuration or combination of components, the following section describes one embodiment of a kit for practicing the present invention:

In some embodiments, the kits of the present invention provide the following reagents:

| CLEAVASE enzyme (e.g., CLEAVASE VIII, CLEAVASE X) | Primary Oligos |
|---|---|
| DNA Reaction Buffer 1 | INVADER Oligo |
|  | FRET Cassette 1 (e.g., F) |
|  | FRET Cassette 2 (e.g., R) |
|  | "No Target" Blank control |

Examples of Primary Oligonucleotides and Secondary Oligonucleotides suitable for use with the methods of the present invention are provided in FIG. 4. While the oligonucleotides shown therein may find use in a number of the methods, and variations of the methods, of the present invention, these INVADER assay oligonucleotide sets find particular use with kits of the present invention. The oligonucleotide sets shown in FIG. 4 may be used as individual sets to detect individual target DNAs, or may be combined in biplex or multiplex reactions for the detection of two or more analytes in a single reaction.

In preferred embodiments, the oligonucleotides shown in FIG. 4 (or similar oligonucleotides) are used in invasive cleavage structure assays (e.g. INVADER assays) to detect alleles in the connexin 26 gene. In preferred embodiments, pools or sets of the assay configurations shown in FIG. 4 are used to simultaneously detect a mutant allele and the corresponding wild-type version of the allele.

It is contemplated that the designs of these probes sets (e.g., the oligonucleotides and/or their sequences) may be adapted for use in RNA detection assays, using the guidelines for reaction design and optimization provided herein. In some embodiments, a kit of the present invention provides a list of additional components (e.g., reagents, supplies, and/or equipment) to be supplied by a user in order to perform the methods of the invention. For example, and without intending to limit such additional components lists to any particular components, one embodiment of such a list comprises the following:

Clear CHILLOUT-14 liquid wax (MJ Research) or RNase-free, optical grade mineral oil (Sigma, Cat. No. M-5904)

96-well polypropylene microplate (MJ Research, Cat. No. MSP-9601)

Sterile 1.5-ml or 2.0-ml microcentrifuge tubes

Sterile, DNase/RNase free disposable aerosol barrier pipet tips

Multichannel pipets (0.5-10 µl, 2.5-20 µl)

Thermal cycler or other heat source (e.g., lab oven or heating block).

Miscellaneous laboratory equipment (tube racks, micropipetors, multichannel pipet, microcentrifuge, vortex mixer).

Fluorescence microplate reader (a preferred plate reader is top-reading, equipped with light filters have the following characteristics:

| Excitation (Wavelength/Bandwidth) | Emission (Wavelength/Bandwidth) |
|---|---|
| 485 nm/20 nm | 530 nm/25 nm |
| 560 nm/20 nm | 620 nm/40 nm |

In some embodiments, a kit of the present invention provides a list of optional components (e.g., reagents, supplies, and/or equipment) to be supplied by a user to facilitate performance of the methods of the invention. For example, and without intending to limit such optional components lists to any particular components, one embodiment of such a list comprises the following:

Sterile 8-tube strip or microplate (optional)

Disposable plastic trough (optional)

Plate sealing tape (optional)

In some embodiments, a kit of the present invention provides a list of required components to be supplied by a user to facilitate performance of the methods of the invention for which multiple alternatives are acceptable (e.g. sample preparation kits). For example, and without intending to limit such optional components lists to any particular components, one embodiment of such a list comprises the following:

QIAGEN QIAAMP Blood Kit

Gentra Systems PUREGENE Kit

Gentra Systems GENERATION Products

In some embodiments of a kit, detailed protocols are provided. In preferred embodiments, protocols for the assembly of INVADER assay reactions (e.g., formulations and preferred procedures for making reaction mixtures) are provided. In particularly preferred embodiments, protocols for assembly of reaction mixtures include computational or graphical aids to reduce risk of error in the performance of the methods of the present invention (e.g., tables to facilitate calculation of volumes of reagents needed for multiple reactions, and plate-layout guides to assist in configuring multi-well assay plates to contain numerous assay reactions). By way of example, and without intending to limit such protocols to any particular content or format, kits of the present invention may comprise the following protocol:

I. DETAILED DNA BIPLEX INVADER ASSAY PROTOCOL

1. Determine the number of samples and controls to be tested.

2. Plan the microplate layout for each experimental run (e.g., samples, controls).Inclusion of a No Target Control (tRNA Carrier in buffered, nuclease-free water) is required for a valid result.

3. Prepare the Invader DNA Assay Reaction Mix for the biplex assay format. To calculate the volumes of reaction components needed for the assay (X Volume), multiply the total number of reactions (samples and controls) by 1.25 (X Volume (µl)=# reactions×1.25). Vortex the Invader DNA Assay Reaction Mix briefly after the last reagent addition to mix thoroughly.

Invader DNA Assay Reaction Mix

Biplex Assay Format

| Reaction Components | 1X Volume | ___X Volume |
|---|---|---|
| DNA Reaction Buffer 1 | 5.0 µl | |
| FRET F Cassette | 1.0 µl | |
| FRET R Cassette | 1.0 µl | |
| Primary Probes | 1.0 µl | |
| INVADER Oligo | 1.0 µl | |
| CLEAVASE enzyme | 1.0 µl | |
| Total Mix Volume (1X) | 10.0 µl | |

4. Add 10 µl of each control or DNA sample (100 ng DNA) to the appropriate well and mix by pipetting up and down 1-2 times. Overlay each reaction with 20 µl of clear CHILLOUT or mineral oil. Seal microplate with Thermaseal well tape (optional).

5. Incubate reactions for 5 minutes at 95° C. in a thermal cycler or oven.

6. Lower the temperature to 63° C. in the thermal cycler or transfer the plate to a 63° C. heat block, then add 10 µl of the INVADER DNA Assay Reaction Mix to each well and mix well by pipetting up and down 3 to 5 times. An 8-tube strip or microplate may be used to facilitate addition of the INVADER DNA Assay Reaction Mix using a multichannel pipet. When adding the INVADER DNA Assay Reaction Mix, be sure to add the mix below the level of the mineral oil or CHILL-OUT 14 liquid wax.

7. Cover the microplate with plate sealing tape (optional) and incubate at 63° C. for 4 hours.

8. After the 4-hour incubation, place the microplate in the plate holder of the fluorescence plate reader. Remove plate sealing tape, if used.

9. Read the plate at the two different wavelength settings (The dye corresponding to the WT and Mut signal is not necessarily the same for all biplex assays).

10. The gain should be set so that Control 4 reads between 100 and 200 for each scan. The Control 4 values do not have to be identical for the F and R dye scans.

NOTE: Remove the microplate seal before reading the microplate.

This procedure enables collection of multiple data sets to extend the assay's dynamic range. During the secondary INVADER reaction, read the microplate directly in a top-reading fluorescence microplate reader.

Recommended settings for a PerSeptive Biosystem Cytofluor 4000 instrument are as follows:

NOTE: Because the optimal gain setting can vary between instruments, adjust the gain as needed to give the best signal/background ratio (sample raw signal divided by the No Target Control signal) or No Target Control sample readings of ~100 RFUs. Fluorescence microplate readers that use a xenon lamp source generally produce higher RFUs. For directly reading the microplates, the probe height of, and how the plate is positioned in, the fluorescence microplate reader may need to be adjusted according to the manufacturer's recommendations.

Calculation of Ratios and Guidelines for Interpretation

In some embodiments, guidelines for using the ratios of the two fluorescent signals to determine a genotype are provided. For example, for each allele of a given polymorphism, the signal/background or Fold Over Zero (FOZ) values may be calculated as follows for the signal obtained with each dye:

$$FOZ = \frac{\text{Raw counts from sample}}{\text{Raw counts from No Target Blank}}$$

The two FOZ values (i.e. wild type and mutant) for each sample were used to calculate the WT:Mut Ratio as follows:

$$\text{Ratio} = \frac{(\text{Net } WT\ FOZ)}{(\text{Net } Mut\ FOZ)}$$

where Net FOZ=FOZ−1

In some embodiments, supplementary documentation, such as protocols for ancillary procedures, e.g., for the preparation of additional reagents, or for preparation of samples for use in the methods of the present invention, are provided. In preferred embodiments, supplementary documentation includes guidelines and lists of precautions provided to facilitate successful use of the methods and kits by unskilled or inexperienced users. In particularly preferred embodiments, supplementary documentation includes a troubleshooting guide, e.g., a guide describing possible problems that may be encountered by users, and providing suggested solutions or corrections intended to aid the user in resolving or avoiding such problems.

For example, and without intending to limit such supplementary documentation to any particular content, kits of the present invention may comprise any of the following procedures and guidelines:

III. SAMPLE PREPARATION

In preferred embodiments, samples are diluted to concentrations that correspond to a 10 μl addition per reaction. Total amounts of genomic DNA added to the reaction may be between 100 ng and 2 μg.

The assay is optimized for performance with genomic DNA samples prepared from whole blood or buffy coat. Several DNA extraction methods/kits have been validated for performance in the Biplex INVADER assay:
  QIAGEN QIAAMP Blood Kit
  Gentra Systems PUREGENE Kit
  Gentra Systems GENERATION Products Quantitation is not necessary if using one of these recommended sample preparation methods (i.e., QIAGEN or Gentra). In other embodiments, the DNA sample should be quantitated. In a preferred embodiment, such quantitation is accomplished using the PICOGREEN or OLIGREEN assay. Quantitating by $A_{260}/A_{280}$ can lead to an overestimation of the amount of DNA in the sample due to RNA contamination. A low $A_{260}/A_{280}$ reading (<1.5) indicates there is an overabundance of protein in the sample. In particularly preferred embodiments, only samples with a concentration >10 ng/μl are used in the INVADER DNA Assay.

In some embodiments, kits of the present invention further include a troubleshooting guide. An exemplary guide is provided below:

| Problem | Possible Solution |
| --- | --- |
| No Signal or Low Signal | Assay:<br>  Mixing inconsistencies. Make sure all reagents are properly mixed prior to assembly of INVADER DNA Assay Reaction Mix. The controls and INVADER DNA Assay Reaction Mixes must be mixed thoroughly and consistently before the plate is set up. During addition of INVADER DNA Assay Reaction Mix to sample plate, mix by pipetting up and down several times, ensuring that all liquid is expelled before removing the tip.<br>  Verify that reagents were added in the correct sequence, to the correct mix, and that the correct mix is added to the appropriate controls/sample wells (refer to sample plate layout).<br>  Verify that all reagents were stored at the proper temperature as indicated in this package insert.<br>  Make sure that 10 μl of the appropriate control was added to each well.<br>  Make sure that the 10 μl of the appropriate INVADER DNA Assay Reaction Mix was added below the level of the mineral oil or CHILL-OUT 14 liquid wax. Not adding the correct amount will result in loss of signal.<br>  Verify that the correct INVADER DNA Assay Reaction Mix is added to the appropriate control.<br>  Make sure assay is run for at five hours at 63° C.<br>  Use mineral oil or clear CHILL-OUT 14 liquid wax to prevent evaporation during the reaction.<br>Instrument:<br>  Verify that the fluorescence plate reader is set to the correct excitation and emission wavelengths for each scan. If possible, run a diagnostic test on the fluorescence plate reader to ensure that the instrument and light source are working properly. Verify that two |

| Problem | Possible Solution |
|---|---|
| | scans were performed at two different wavelengths.<br>Make sure the proper "96-well plate type" has been selected in the fluorescence plate reader.<br>Verify that the coordinates of the plate are programmed correctly in the fluorescence plate reader. Signal should be read in the middle of the well and at an optimal distance from the plate for best results.<br>Incubations should be conducted in properly calibrated heating units. Checking these units on a regular basis using a thermocouple thermometer equipped with a probe traceable to NIST standards is recommended.<br>Make sure that the plate is firmly seated in the thermal cycler or heat block. |
| High Signal in Control 4 (No Target Blank) | Assay:<br>Use DNase/RNase free aerosol barrier tips and sterile tubes for making the INVADER DNA Assay Reaction Mix.<br>Make sure that pipet tips are changed after each use.<br>Wear gloves when setting up the assay.<br>Make sure that pipet tips do not touch any other surfaces except the solution being pipetted, since nucleases may be present.<br>Do not touch pipet tips with hands.<br>Instrument:<br>Adjust the gain setting of the fluorescence plate reader such that Control 4 (No Target Blank) reads approximately 200 for each scan. |
| Fluorescent Signal Is Off-scale | Assay:<br>Use DNase/RNase free aerosol barrier tips and sterile tubes for making the INVADER DNA Assay Reaction Mix.<br>Confirm that the incubations were done for the correct amount of time and at the correct temperature.<br>Instrument:<br>Adjust the gain of the fluorescence plate reader. The gain of the two scans should be set so that Control 4 (No Target Blank) reads at least 100 for each scan; however, an approximate level of 200 is recommended.<br>Allow the lamp in the fluorescence plate reader to warm up for at least 10 minutes before reading the results. |

EXPERIMENTAL

The following examples are provided in order to demonstrate and further illustrate certain preferred embodiments and aspects of the present invention and are not to be construed as limiting the scope thereof. The following abbreviations are used: Ex. (Example); Fig. (Figure); ° C. (degrees Centigrade); g (gravitational field); hr (hour); min (minute); olio (oligonucleotide); rxn (reaction); vol (volume); w/v (weight to volume); v/v (volume to volume); BSA (bovine serum albumin); CTAB (cetyltrimethylammonium bromide); HPLC (high pressure liquid chromatography); DNA (deoxyribonucleic acid); p (plasmid); µl (microliters); ml (milliliters); µg (micrograms); mg (milligrams); M (molar); mM (milliMolar); µM (microMolar); pmoles (picomoles); amoles (attomoles); zmoles (zeptomoles); nm (nanometers); kdal (kilodaltons); OD (optical density); EDTA (ethylene diamine tetra-acetic acid); FITC (fluorescein isothiocyanate); SDS (sodium dodecyl sulfate); NaPO$_4$ (sodium phosphate); NP-40 (Nonidet P-40); Tris (tris(hydroxymethyl)-aminomethane); PMSF (phenylmethylsulfonylfluoride); TBE (Tris-Borate-EDTA, i.e., Tris buffer titrated with boric acid rather than HCl and containing EDTA); PBS (phosphate buffered saline); PPBS (phosphate buffered saline containing 1 mM PMSF); PAGE (polyacrylamide gel electrophoresis); Tween (polyoxyethylene-sorbitan); Red (REDMOND RED Dye, (Synthetic Genetics, San Diego, Calif.) Z28 (ECLIPSE Quencher, (Synthetic Genetics, San Diego, Calif.); ATCC (American Type Culture Collection, Rockville, Md.); Coriell (Coriell Cell Repositories, Camden, N.J.); DSMZ (Deutsche Sammlung von Mikroorganismen und Zellculturen, Braunschweig, Germany); Ambion (Ambion, Inc., Austin, Tex.); Boehringer (Boehringer Mannheim Biochemical, Indianapolis, Ind.); MJ Research (MJ Research, Watertown, Mass.; Sigma (Sigma Chemical Company, St. Louis, Mo.); Dynal (Dynal A. S., Oslo, Norway); Gull (Gull Laboratories, Salt Lake City, Utah); Epicentre (Epicentre Technologies, Madison, Wis.); Lampire (Biological Labs., Inc., Coopersberg, Pa.); MJ Research (MJ Research, Watertown,Mass.); National Biosciences (National Biosciences, Plymouth, Minn.); NEB (New England Biolabs, Beverly, Mass.); Novagen (Novagen, Inc., Madison, Wis.); Perkin Elmer (Perkin-Elmer/ABI, Norwalk, Conn.); Promega (Promega, Corp., Madison, Wis.); Stratagene (Stratagene Cloning Systems, La Jolla, Calif.); Clonetech (Clonetech, Palo Alto, Calif.) Pharmacia (Pharmacia, Piscataway, N.J.); Milton Roy (Milton Roy, Rochester, N.Y.); Amersham (Amersham International, Chicago, Ill.); and USB (U.S. Biochemical, Cleveland, Ohio). Glen Research (Glen Research, Sterling, Va.); Gentra (Gentra, Minneapolis, Minn.); Third Wave Technologies (Third Wave Technologies, Madison, Wis.); PerSeptive Biosystems (PerSeptive Biosystems, Framington, Mass.); Microsoft (Microsoft, Redmond, Wash.); Qiagen (Qiagen, Valencia, Calif.); Molecular Probes (Molecular Probes, Eugene, Oreg.); VWR (VWR Scientific,); Advanced Biotechnologies (Advanced Biotechnologies, INC., Columbia, Md.).

EXAMPLE 1

Detection of the 30ΔG Mutation is Connexin 26 (GJB2)

This example describes detection of the 30ΔG, also referred to as the "35ΔG" mutation, as well as the corresponding wild type sequence, in genomic DNA isolated from blood samples using the INVADER assay. This example demonstrates that the INVADER assay can readily discriminate homozygous wild type, heterozygous, and homozygous mutant genotypes at this locus. This example further demonstrates that various sample preparation procedures are compatible with detection using the Invader assay.

i. Sample Preparation

To determine the compatibility of the INVADER assay with different sample preparation methods, four sample preparation techniques were tested: Gentra Systems PURE-GENE Kit, Gentra Systems GENERATION Products, QIAGEN QIAAMP Blood Kit from buffycoat or from whole blood.

30ΔG, containing hexanediol as a 3' blocking group. SEQ ID NO:2 (5'-TCCGCGCGTCCCCCAGGATCGTCTG-hexanediol-3') is a probe oligonucleotide specific for the 30ΔG variant, containing hexanediol as a 3' blocking group. SEQ ID NO:3 (5'-TGCTGGTGGAGTGTTTGTTCACACCA-3') is an INVADER oligonucleotide for use in detecting either allele. SEQ ID NOs: 4 and 5 are partial genomic DNA sequences in the region of the wild type and mutant versions of the connexin 26 gene, respectively, targeted by SEQ ID NOs: 1-3.

INVADER assays were set up to detect wild type and variant versions of the connexin 26 gene at nucleotide 30. Target DNA was provided as a genomic DNA prepared as described above. Biplex INVADER reactions (e.g. as shown in FIG. 1) were carried out in a final volume of 20 μl in a 96-well microplate. Aliquots of 10 μl of each sample (genomic DNA, final amounts ranging between 20 ng to 2 μg per reaction) or no target control (10 ng/μl tRNA) were added to the appropriate wells and then overlaid with 20 μl mineral oil. Samples were denatured at 95° C. for 5 minutes and then cooled to 63° C. A 10 μl aliquot of the following INVADER reaction mix was then added to each well and mixed by pipetting:

| Component | Amount per reaction | Final concentrations |
|---|---|---|
| DNA reaction buffer 1 (14% PEG, 40 mM MOPS, pH 7.5, 56 mM MgCl$_2$, 0.02% ProClin 300) | 5 μl | 3.5% PGE, 10 mM MOPS, 14 mM MgCl$_2$ |
| INVADER oligo (1 μM) | 1 μl | 1 pmol |
| Primary Probes (20 μM) | 1 μl | 10 pmol each |
| FAM FRET (5 μM) SEQ ID NO: 6 [5'-(FAM)TCT(Z28)AGCCGGTTTTCCGGCTGA GACCTCGGCGCG-hexanediol-3')] | 1 μl | 5 pmol |
| RED FRET (5 μM) SEQ ID NO: 7 [5'-(RED)TCT(Z28)AGCCGGTTTTCCGGCTGA GAGGACGCGCGGA-hexanediol-3')] | 1 μl | 5 pmol |
| CLEAVASE X enzyme (40 ng/μl) in CLEAVASE dilution buffer | 1 μl | 40 ng |

Each kit was used according to the manufacturer's protocols using approximately 6 ml of blood or 200 μl of buffycoat.

In addition, 12 genomic samples were obtained from an outside source that had been prepped by the outside sourse. An additional genomic sample was obtained from Coriell Cell Repositories, Camden, N.J., corresponding to catalog number NT14640.

ii. INVADER Assay Reagents and Methods

In this example, SEQ ID NOs:1-2 were employed as probe oligonucleotides in the INVADER assays (as described below). For each of these sequences, the 5' portion ("flap") is highlighted with underlining. The remaining non-underlined part of the sequences is the 3' portion (Target Specific Region). Also, fragments that would be generated during an invasive cleavage reaction with these sequences (and the indicated INVADER oligonucleotides shown below) are the underlined sequence (5' portion) plus the first base (in bold) from the 3' portion. These fragments are designed to participate in a second invasive cleavage reaction with a FRET cassette by serving as the INVADER (upstream) oligonucleotide in this second invasive cleavage reaction. SEQ ID NO:1 (5'-CGCGCCGAGGCCCCAGGATCGTCT-hexanediol-3') is a probe oligonucleotide specific for the wild-type allele of Reactions were incubated at 63° C. for 4 hours and then cooled to 4° C. prior to scanning in a CYTOFLUOR 4000 fluorescence plate reader (Applied Biosystems, Foster City, Calif.). The settings used were: 485/20 nm excitation/bandwidth and 530/25 mn emission/bandwidth for F dye detection, and 560/20 nm excitation/bandwidth and 620/40 nm emission/bandwidth for R dye detection. The instrument gain was set for each dye so that the No Target Blank produced between 100-200 Absolute Fluorescence Units (AFUs).

The raw data that is generated by the device/instrument is used to measure the assay performance (real-time or endpoint mode). The equations below provide how FOZ, and other values are calculated. NTC in the equations below represents the signal from the No Target Control. Also, FOZ is an abbreviation for fold over zero.

Figure 2:
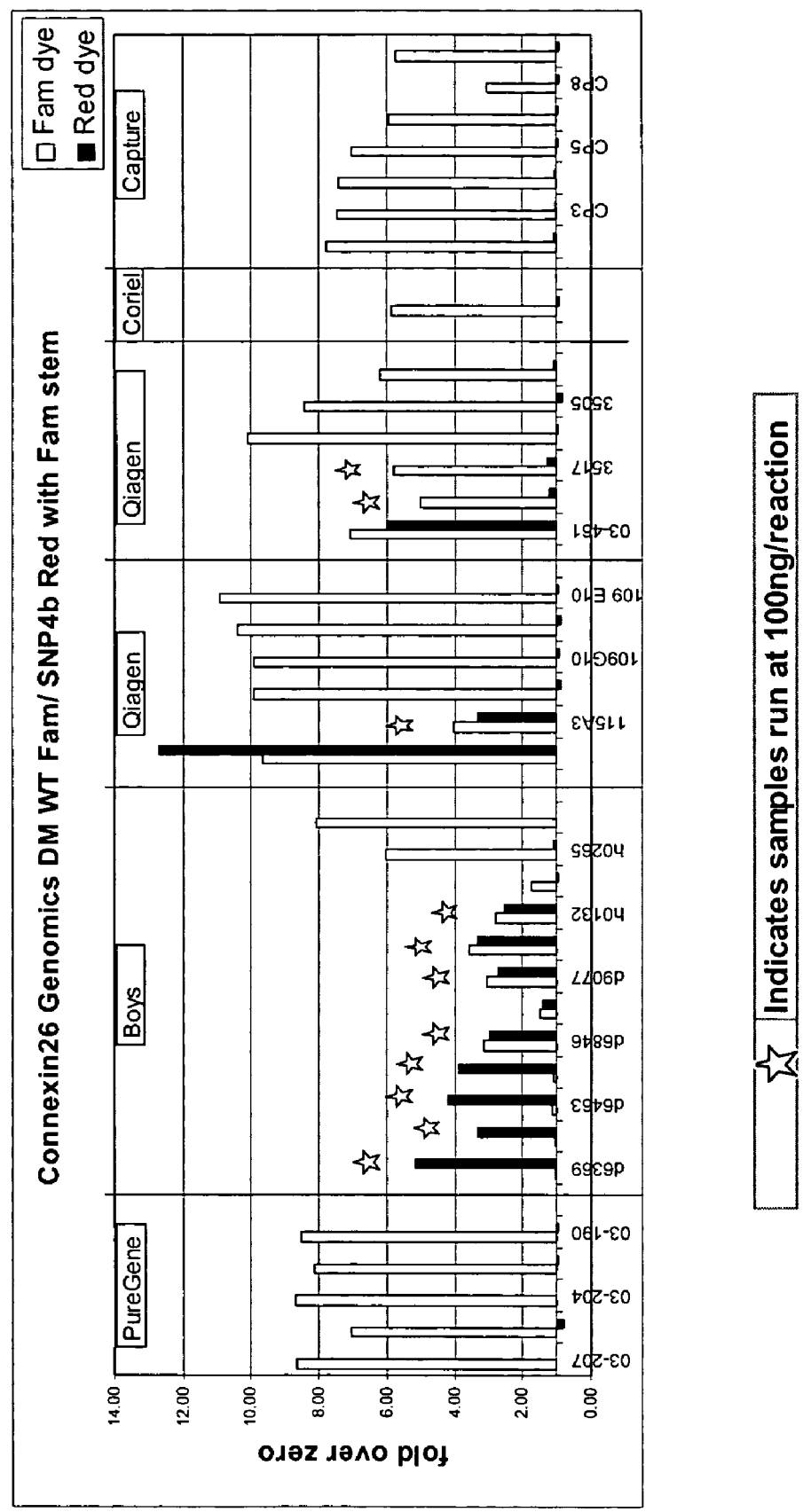
FIG. 2 shows results of experiments designed to detect the presence of the 30ΔG or wild-type sequence of connexin 26.

FOZ or Signal/No Target $FOZ_{Dye1} = (RawSignal_{Dye1}/NTC_{Dye1})$ $FOZ_{Dye2} = (RawSignal_{Dye2}/NTC_{Dye2})$ The results of these experiments are presented in FIG. 2. The samples are aligned along the X-axis and grouped according to the procedure used to purify the genomic DNA from the specimen. The FOZ for each dye is indicated along the Y-axis as denoted in the legend. Samples containing 100 ng of genomic DNA target are indicated by stars above the histograms. These results indicate that the INVADER assay discriminated wild-type samples from heterozygotes and mutants homozygous for the 30ΔG allele. All but two of the heterozygous samples had FAM/RED dye ratios between 0.89 and 1.28, where 1 would indicate equal quantities of signal generated from each allele. The two samples outside this range both contained high levels of DNA, resulting in artifactual skewing of the ratios of the signals. It has been observed elsewhere that at high signal levels, the signal from the FAM dye saturates at a lower level than does that from the RED dye.

These results further demonstrate that all of the various sample preparations procedures were compatible with the INVADER assay and that significant variation in signal level correlated with the amount of target genomic DNA added to the reactions.

EXAMPLE 2

Detection of the 167ΔT Mutation in Connexin 26 (GJB2)

This example describes detection of the 167ΔT mutation, as well as the corresponding wild-type sequence, in genomic DNA isolated from blood samples using the INVADER assay. This example demonstrates that the INVADER assay can readily discriminate homozygous wild type, heterozygous, and homozygous mutant genotypes at this locus. This example further demonstrates that various sample preparation procedures are compatible with detection using the Invader assay.

i. Sample Preparation

To determine the compatibility of the INVADER assay with different sample preparation methods, two sample preparation techniques were tested: Gentra Systems PUREGENE Kit was used to purify genomic DNA from whole blood and QIAGEN QIAAMP Blood Kit from was used to purify genomic DNA from buffycoat.

Each kit was used according to the manufacturer's protocols using approximately 6 mls of blood or 200 µl of buffycoat.

ii. INVADER Assay Reagents and Methods

In this example, SEQ ID NOs:10-11 were employed as probe oligonucleotides in the INVADER assays (as described below). For each of these sequences, the 5' portion ("flap") is highlighted with underlining. The remaining non-underlined part of the sequences is the 3' portion (Target Specific Region). Also, fragments that would be generated during an invasive cleavage reaction with these sequences (and the indicated INVADER oligonucleotides shown below) are the underlined sequence (5' portion) plus the first base (in bold) from the 3' portion. These fragments are designed to participate in a second invasive cleavage reaction with a FRET cassette by serving as the INVADER (upstream) oligonucleotide in this second invasive cleavage reaction. SEQ ID NO:10 (5'-ACGGACGCGGAGCAGGGTGTTGCAGAC-hexanediol-3') is a probe oligonucleotide specific for the wild-type allele of 167ΔT. SEQ ID NO:11 (5'-AGGCCACGGACGCGGGTGTTGCAGAC-hexanediol-3') is a probe oligonucleotide specific for the 167ΔT variant. SEQ ID NO:12 (5'-ATCGTAGCACACGTTCTTGCAGC-CTGGCTGA-3') is an INVADER oligonucleotide for use in detecting either allele at nucleotide 167.

INVADER assays were set up to detect wild type and variant versions of the connexin 26 gene at nucleotide 167. Target DNA was provided as a genomic DNA prepared as described above. Duplicate biplex INVADER reactions (e.g. as shown in FIG. 1) were carried out in a final volume of 20 µl in a 96-well microplate as described in Example 1. The FRET probes used were SEQ ID NOs:13 (5'-(FAM)-TCT(Z28) AGC CGG TTT TCC GGC TGA GAC TCC GCG TCC GT-hexanediol) and 14 (5'-(RED)-TCT(Z28)TCG GCC TTT TGG CCG AGA GAC GTC CGT GGC CT-hexanediol-3'). Aliquots of 10 µl of each sample containing a total of 100 ng of genomic DNA or no target control (10 ng/µl tRNA) were added to the appropriate wells and then overlaid with 30 µl mineral oil. Aliquots of 10 µl of an INVADER reaction mix were added, the reactions run, and the signal detected as described in Example 1.

Figure 3:
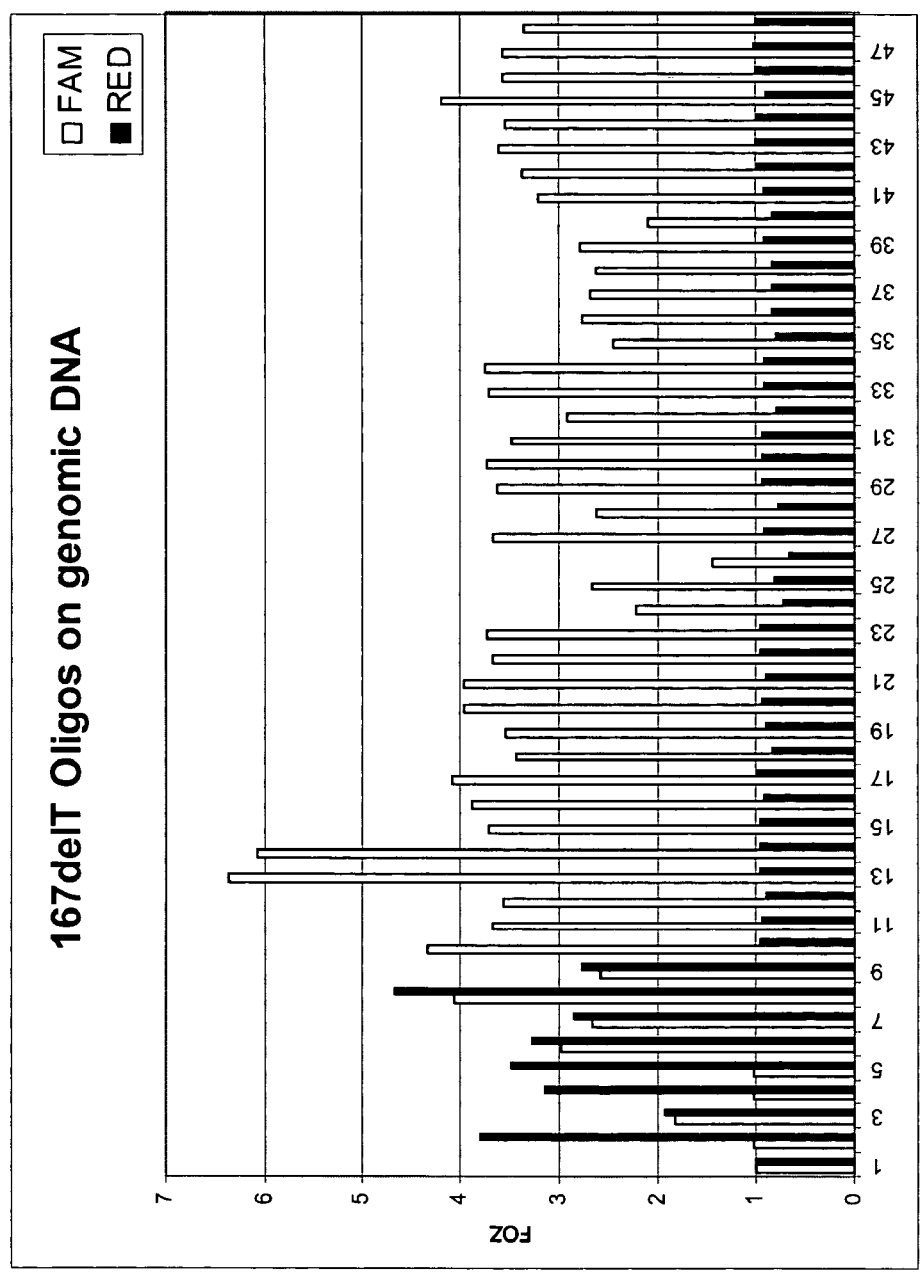
FIG. 3 shows the results of experiments designed to detect the presence of the 167ΔT or wild-type sequence of connexin 26.

The results of these experiments are presented in FIG. 3. The samples are aligned along the X-axis. The FOZ for each dye is indicated along the Y-axis as denoted in the legend. These results indicate that the INVADER assay discriminated wild-type samples from heterozygotes and mutants homozygous for the 167ΔT allele. These results further demonstrate that all of the various sample preparations procedures were compatible with the INVADER assay.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A kit for characterizing a target sequence for the presence or absence of Connexin 26 allele 30ΔG, wherein said kit comprises first and second oligonucleotides configured to form an invasive cleavage structure when in combination with said target sequence, wherein said first oligonucleotide comprises a 5' portion and a 3' portion, wherein said 3' portion of said first oligonucleotide comprises the sequence 5' CCCAGGATCGTCTG 3' (SEQ ID NO:15) or 5' CCCCAGGATCGTCT 3' (SEQ ID NO:17) configured to hybridize to said target sequence, and wherein said 5' portion of said first oligonucleotide is configured to not hybridize to said target sequence, and wherein said second oligonucleotide comprises a 5' portion and a 3' portion, wherein said 5' portion of said second oligonucleotide comprises the sequence 5' TGCTGGTGGAGTGTTTGTTCACACC 3' (SEQ ID NO:16) configured to hybridize to said target sequence, and wherein said 3' portion of said second oligonucleotide is configured to not hybridize to said target sequence.

2. The kit of claim 1, wherein said kit comprises a plurality of first oligonucleotides, where said plurality of first oligonucleotides comprises a first first oligonucleotide comprising a 5' portion and a 3' portion, wherein said 3' portion of said first first oligonucleotide comprises the sequence 5' CCCAGGATCGTCTG 3' (SEQ ID NO:15) configured to hybridize to a target sequence comprising a Connexin 26 allele , and wherein said 5' portion of said first first oligonucleotide is configured to not hybridize to said target sequence, and a second first oligonucleotide comprising a 5' portion and a 3' portion, wherein said 3' portion of said second first oligonucleotide comprises the sequence 5' CCCCAGGATCGTCT 3' (SEQ ID NO:17) configured to hybridize to a target sequence comprising a Connexin 26 allele, and wherein said 5' portion of said second first oligonucleotide is configured to not hybridize to said target sequence.

3. The kit of claim 1, further comprising a cleavage agent, wherein said cleavage agent is a 5' nuclease.

4. The kit of claim 3, wherein said 5' nuclease comprises a FEN-1 endonuclease.

5. The kit of claim 3, wherein said 5' nuclease comprises a polymerase.

6. The kit of claim 1, further comprising instructions for using said kit for said detecting the presence or absence of Connexin 26 allele 30ΔG.

7. The kit of claim 6, wherein said instructions comprise instructions required by the United States Food and Drug Administration for labeling of analyte specific reagents.

8. The kit of claim 6, wherein said instructions comprise instructions required by the United States Food and Drug Administration for labeling of in vitro diagnostics.

9. The kit of claim 1, further comprising a FRET probe comprising a portion that is complementary to said 5' portion of said first oligonucleotide.

10. The kit of claim 2, further comprising a plurality of FRET probes, wherein said plurality of FRET probes comprises a first FRET probe comprising a portion that is complementary to said 5' portion of said first first oligonucleotide, and a second FRET probe comprising a portion that is complementary to said 5' portion of said second first oligonucleotide.

11. The kit of claim 10, wherein said first FRET probe and said second FRET probe have different labels from each other.

* * * * *

SEQUENCE LISTING

<160> NUMBER OF SEQ ID NOS: 17

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
cgcgccgagg ccccaggatc gtct                                           24

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
tccgcgcgtc ccccaggatc gtctg                                          25

<210> SEQ ID NO 3
<211> LENGTH: 26
<212> TYPE: DNA
<213> ORGANISM: Artificial Sequence
<220> FEATURE:
<223> OTHER INFORMATION: Synthetic

<400> SEQUENCE: 3
tgctggtgga gtgtttgttc acacca                                         26

<210> SEQ ID NO 4
<211> LENGTH: 61
<212> TYPE: DNA
<213> ORGANISM: Artificial Sequence
<220> FEATURE:
<223> OTHER INFORMATION: Synthetic

<400> SEQUENCE: 4
gggcacgctg cagacgatcc tgggggtgt gaacaaacac tccaccagca ttggaaagat     60
c                                                                    61

<210> SEQ ID NO 5
<211> LENGTH: 60
<212> TYPE: DNA
<213> ORGANISM: Artificial Sequence
<220> FEATURE:
<223> OTHER INFORMATION: Synthetic

<400> SEQUENCE: 5
gggcacgctg cagacgatcc tggggtgtg aacaaacact ccaccagcat tggaaagatc     60

<210> SEQ ID NO 6
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The residue at this position is linked to a Z28
      quenching group.

<400> SEQUENCE: 6
tctagccggt tttccggctg agacctcggc gcg                                 33

<210> SEQ ID NO 7
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)

```
<223> OTHER INFORMATION: The residue at this position is linked to a Z28
      quenching group.

<400> SEQUENCE: 7
tctagccggt tttccggctg agaggacgcg cgga                                      34

<210> SEQ ID NO 8
<211> LENGTH: 11
<212> TYPE: DNA
<213> ORGANISM: Artificial Sequence
<220> FEATURE:
<223> OTHER INFORMATION: Synthetic

<400> SEQUENCE: 8
cgcgccgagg c                                                               11

<210> SEQ ID NO 9
<211> LENGTH: 12
<212> TYPE: DNA
<213> ORGANISM: Artificial Sequence
<220> FEATURE:
<223> OTHER INFORMATION: Synthetic

<400> SEQUENCE: 9
tccgcgcgtc cc                                                              12

<210> SEQ ID NO 10
<211> LENGTH: 27
<212> TYPE: DNA
<213> ORGANISM: Artificial Sequence
<220> FEATURE:
<223> OTHER INFORMATION: Synthetic

<400> SEQUENCE: 10
acggacgcgg agcagggtgt tgcagac                                              27

<210> SEQ ID NO 11
<211> LENGTH: 26
<212> TYPE: DNA
<213> ORGANISM: Artificial Sequence
<220> FEATURE:
<223> OTHER INFORMATION: Synthetic

<400> SEQUENCE: 11
aggccacgga cgcgggtgtt gcagac                                               26

<210> SEQ ID NO 12
<211> LENGTH: 31
<212> TYPE: DNA
<213> ORGANISM: Artificial Sequence
<220> FEATURE:
<223> OTHER INFORMATION: Synthetic

<400> SEQUENCE: 12
atcgtagcac acgttcttgc agcctggctg a                                         31

<210> SEQ ID NO 13
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The residue at this position is linked to a Z28
      quenching group.
```

```
<400> SEQUENCE: 13
tctagccggt tttccggctg agactccgcg tccgt                              35

<210> SEQ ID NO 14
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The residue at this position is linked to a Z28
      quenching group.

<400> SEQUENCE: 14
tcttcggcct tttggccgag agacgtccgt ggcct                              35

<210> SEQ ID NO 15
<211> LENGTH: 14
<212> TYPE: DNA
<213> ORGANISM: Artificial Sequence
<220> FEATURE:
<223> OTHER INFORMATION: Synthetic

<400> SEQUENCE: 15
cccaggatcg tctg                                                     14

<210> SEQ ID NO 16
<211> LENGTH: 25
<212> TYPE: DNA
<213> ORGANISM: Artificial Sequence
<220> FEATURE:
<223> OTHER INFORMATION: Synthetic

<400> SEQUENCE: 16
tgctggtgga gtgtttgttc acacc                                         25

<210> SEQ ID NO 17
<211> LENGTH: 14
<212> TYPE: DNA
<213> ORGANISM: Artificial Sequence
<220> FEATURE:
<223> OTHER INFORMATION: Synthetic

<400> SEQUENCE: 17
ccccaggatc gtct                                                     14
```